(12) United States Patent
Willing et al.

(10) Patent No.: US 7,414,727 B2
(45) Date of Patent: Aug. 19, 2008

(54) GAS DETECTION METHOD AND GAS DETECTION DEVICE

(75) Inventors: Bert Willing, Blonay (CH); Markus Kohli, Grandson (CH); Andreas Seifert, Denens (CH)

(73) Assignee: IR Microsystems SA, Lausanne (CH)

( * ) Notice: Subject to any disclaimer, the term of this patent is extended or adjusted under 35 U.S.C. 154(b) by 208 days.

(21) Appl. No.: 11/413,473

(22) Filed: Apr. 28, 2006

(65) Prior Publication Data
US 2007/0255508 A1 Nov. 1, 2007

(51) Int. Cl.
*G01N 21/00* (2006.01)

(52) U.S. Cl. .......................... 356/437; 356/438
(58) Field of Classification Search ......... 250/573–575, 250/339.11–33, 338.5; 356/432–442
See application file for complete search history.

(56) References Cited

U.S. PATENT DOCUMENTS

| | | | |
|---|---|---|---|
| 5,267,019 | A | 11/1993 | Whittaker et al. |
| 6,040,914 | A | 3/2000 | Bortz et al. |
| 6,356,350 | B1 | 3/2002 | Silver et al. |
| 7,116,422 | B2 | 10/2006 | Larking et al. |
| 7,180,595 | B2 | 2/2007 | Willing et al. |

FOREIGN PATENT DOCUMENTS

JP 58223041 12/1983

*Primary Examiner*—Gregory J Toatley, Jr.
*Assistant Examiner*—Tri T Ton
(74) *Attorney, Agent, or Firm*—Bachman & LaPointe, P.C.

(57) ABSTRACT

A method for etalon suppression in a gas detection device by determining an etalon fringe period during a calibration step without gas in dependency of the DC drive current. A measuring signal which is a function of the gas absorption and substantially independent of an intensity modulation of an initial light signal at an initial frequency (f) is generated by determining a first pre-measuring signal when the laser source is operated at the center of the gas absorption peak, a second pre-measuring signal when the laser source is operated with a DC drive current below the gas absorption peak of the gas to be detected, and a third pre-measuring signal when the laser source is operated with a DC drive current above said gas absorption peak, with a difference between said DC drive currents which corresponds to the etalon fringe period determined in a calibration step before. The final measuring signal is determined as the difference between the first pre-measuring signal and the arithmetic mean of the second pre-measuring signal and the third pre-measuring signal.

4 Claims, 5 Drawing Sheets

GAS DETECTION METHOD AND GAS DETECTION DEVICE

BACKGROUND OF THE INVENTION

The present invention concerns in particular low-cost infrared (IR) gas detection as disclosed in WO 2005/026705 A1.

The gas detection method and gas detector device as described in this prior art publication is based on a source formed by a wavelength modulated Vertical Cavity Surface Emitting Laser (VCSEL) or Distributed FeedBack (DFB) laser and uses the fact that the modulation of the wavelength is directly connected to a modulation of the laser source output intensity. The intensity of the light having passed the gas volume and being incident to the detector therefore shows a first modulation related to the laser source intensity and a second modulation related to the gas absorption as the wavelength is scanned across the gas absorption line. Accordingly, the known detection method and device provides an initial light signal by a wavelength modulated laser source.

The source provides an initial light signal, which is wavelength modulated with an AC modulation signal at a given initial frequency (f) at the absorption line around the gas to be determined. A light sensor respectively is arranged at the periphery of a detection region intended for receiving at least a gas the concentration of which is to be determined. The light sensor receives a resulting light signal formed by the initial light signal having passed through the detection region. In the following a detection signal is formed which is substantially proportional to the time derivate of the resulting light signal. Further disclosed are first means for generating a first modulation reference signal at the given frequency (f) and second means for generating a second modulation reference signal at twice this frequency (2f). The detection signal is multiplied by the first modulation reference signal and then integrated over time in order to provide a first measuring signal which is a function of the intensity of said initial light signal and substantially independent of the concentration of said gas. The detection signal is further multiplied by said second modulation reference signal and then integrated over time in order to provide a second measuring signal which is a function of the gas absorption and substantially independent of an intensity modulation of the initial light signal at the given initial frequency. The final measuring signal is then received by dividing the second measuring signal by the first measuring signal, thereby providing a signal relative to the concentration or the presence of a given gas. This gas detector method and device have the advantage that only a single sensor unit is needed for one laser source. All necessary information for determining a precise gas concentration value is given by the processing of the generated detection signal which is proportional to the derivate of the light signal received by the sensor unit after having passed through a sample of the defined gas.

The first and second reference modulation signal both are in phase with the intensity variations of the initial light signal. With this known measurement technique the detector signal is time derivated, and the derivated signal is fed into a two-channel lock-in amplifier. The first channel operates on the modulation frequency f, and the output signal is proportional to the slope of the optical power as function of the laser current. The second channel operates of twice the modulation frequency and its output gives a signal, which is proportional to the gas concentration encountered by the laser beam. The ratio of the measuring signal at the frequency 2f to the measuring signal at the frequency f gives the absolute concentration of the gas independent of the laser output as the measuring signal at the frequency f contains information about the laser intensity under the assumption that variations of the laser intensity stem from optical degradations in the light path, such as dust, condensation, speckles. This assumption only holds for two conditions:

1. The laser does not show mode hopping, i.e. sudden changes of wavelength. If such a mode hopping occurs, the wavelength has to be re-adjusted by a change of the DC laser current, which in turn changes the laser output power. With a VCSEL the slope, which is measured by the signal at the frequency f does not necessarily change accordingly. In the case of a DFB laser, the output power is strictly proportional to the DC current which gives the same signal at the frequency f for different output powers.

2. The temperature of the laser is exactly stabilized. For a change of the laser temperature, the wavelength changes, which in turn leads to a re-adjustment of the DC laser current to stay centered on the wavelength of the gas absorption line. Such a change of the current means an intensity change as described in item 1.

With the method described in the prior art patent application, the signal based on a modulation reference signal at the frequency f shows a slope around the center of the gas absorption line, which is proportional to the gas concentration. At high gas concentrations, the accuracy of the measurement is limited by the accuracy of the DC laser current of which the error influences the modulation reference signal at the frequency f. Variations of the current will cause variation of the laser signal, and this effect increases with concentration. This shows, that for some applications this prior art method and device is quite demanding in terms of temperature control of the laser, and depends very much on the thermal mounting of the latter. DFB lasers and VCSEL's differ very much in their thermal budget so that the tracking of the gas absorption line, which is always necessary in term of DC current, has to include a temperature tracking as well.

The co-pending U.S. patent application Ser. No. 11/227,477 describes a first modulation reference signal at twice of said initial frequency is generated by respective means, whereby said first modulation reference signal has a 45° phase angle to said initial light signal. This first modulation reference signal oscillates at an amplitude level between amplitude levels 1 and 0 and is different from the amplitude level of the second modulation reference signal. Finally the detection signal directly received from the resulting light signal is multiplied with the first modulation reference signal. Thus, the first modulation reference signal is not measured on the frequency f, but on the frequency 2f with a slight modification of the 2f modulation reference signal in the amplitude levels and a phase shifting of 45° between the first modulation reference signal and the initial frequency, which is necessary to provide the same phase which is obtained by a derivate over time. Further, the detector signal is no longer derivated but directly fed to the lock-in amplifier for generating a first measuring signal, which is a function of the intensity of the initial light signal. The resulting signal is directly proportional to the light intensity of the laser as seen by the detector without gas absorption (i.e. including any degradations of the light beam between laser and detector). Further it is proposed to combine this first 2f modulation reference signal and its signal treatment with other treatments in order to obtain stable final measuring signals dependent on the special application of gas detection. In a further embodiment, the second modulation reference signal is generated at twice of said initial frequency f, whereby the first and second modulation reference signals have the same phase correlation to the initial light signal; therefore both signals have 45° phase angle to the AC modulation signal for the laser source. Further, the second modulation reference signal oscillates between amplitude levels 1 and −1. For generating the second measuring signal the detection signal directly received from the resulting light signal is multiplied via lock-in amplifier with said second modulation reference signal. The final measuring signal is obtained by the above-mentioned ratio. In this embodiment the final measuring signal is obtained by a first and a second measuring signal based on a 2f modulation reference signal, both obtained with a detection signal directly received from the resulting light signal. In an other embodiment the second modulation reference signal is generated at twice of said initial frequency f, whereby said second modulation reference signal is exactly in phase with the intensity variations of said initial light signal. The detection signal generated by said detection means is substantially proportional to the time derivate of said resulting light signal and the second measuring signal is generated by multiplying said detection signal with said second modulation reference signal. This signal treatment shows the best result, which is independent from the laser temperature and sudden wavelength changes. In this embodiment also the final measuring signal is obtained by a first and a second measuring signal based on a 2f modulation reference signal, but the second measuring signal, which is a function of the absorption is obtained with a derivated detection signal. In a further embodiment, which needs more electronic parts, two reference modulation signals at a frequency f and 2f are used for generating two measuring signals, which are a function of intensity of the initial light signal. This is realised by generating, additionally to the first measuring signal based on the first 2f modulation reference signal, a third measuring signal, which is also a function of intensity of said initial light signal. This third measuring signal is generated from a detection signal by multiplying the detection signal with a third modulation reference signal at the initial frequency f and then integrated over time. Further the second measuring signal is generated from said detection signal, by multiplying said detection signal with a second 2f modulation reference signal at twice of said initial frequency f and then integrated over time. The third and second modulation reference signals are exactly defined in phase with the intensity variations of said initial light signal and the detection signal for both measuring signals are substantially proportional to the time derivate of the resulting light signal. The final measuring signal is obtained by correlating the first and third measuring signal and generating the ratio between the second measuring signal and the correlated signal of the first and second measuring signal.

Generally speaking, in wavelength modulation laser spectrometry, the laser wavelength is modulated at a modulation frequency f. After transmission of the light through the gas sample to be measured, the laser light is incident onto a photo detector. In general, the signal of the photo detector is fed into a phase-sensitive lock-in amplifier and the gas concentration is related to the photo detector signal on twice the modulation frequency (2f detection).

The 2f detection is limited by various noise sources: laser intensity noise (which partly can be compensated for by measuring the laser intensity);

electronic noise stemming from the photo detector and/or the amplifying circuitry;

optical interference-based noise.

The optical noise based on interference can take the form of speckles or of etalon fringes. Speckles are interference patterns created by the diffraction of the coherent laser light at irregularities like dust, dirt etc. Speckles are not the object of this invention.

Etalon fringes are caused by portions of the light, which are back-reflected from optical interfaces within the designed light path (i.e. windows, lenses, mirrors etc.). As the back-reflected parts of the laser light are in coherence with the laser beam, the interaction of back-reflection and propagating laser light can create a standing wave within the cavity of the gas absorption device (i.e. the free-space absorption path containing the gas to be measured).

If the length of the cavity is changed, the amplitude of the standing wave at the location of the photo detector will vary between periodical minima and maxima as a function of the cavity length. The same effect can be obtained if the cavity length is held constant and the wavelength of the laser light is changed. The periodical variation of the light amplitude with cavity length or with laser wavelength is called "etalon fringes". FIG. 1 shows in diagram (a) etalon fringes of a methane gas detector with zero gas concentration (note that the electronic noise floor is not resolved in this graph) and in diagram (b) the same device as in (a) with methane present. The etalon fringes are about the same size as the gas absorption signal at the center of the absorption peak.

In a real-world gas detection device, the variation of the length of the cavity stems from thermal expansion of its mechanical members. As an example, with a thermal expansion coefficient of steel (10 ppm/°C.), a mechanical length of 10 cm and a temperature of operation from 0° C. to 50° C., the cavity changes its length by 5 micrometers. This variation of length corresponds to 3 to 4 times the laser wavelength and can therefore create massive etalon fringes. The etalon fringes are not directly correlated to the intensity of the laser and can therefore not be compensated by measuring the laser intensity.

The period of the etalon fringes on the ambient temperature or the laser wavelength (drive current) is a function of the length of the geometrical cavity, which creates the etalon fringes: The longer the cavity, the shorter the etalon fringe period. For a gas detection device based on a Vertical Cavity Surface Emitting Laser (VCSEL), the etalon fringe period is on the same order than the gas absorption peak (in wavelength) if the etalon fringe generating cavity has a length of several centimeters, which is the typical length of an absorption path. Very small cavities, i.e. the window of the laser cap, generate etalon fringes, which have periods longer than the entire tuning range of the VCSEL. In such a case, the signal variations with ambient temperature resemble a change of the signal offset.

A gas detection device will always contain optical interfaces (at least the laser chip will be sealed hermetically underneath an optical window), and operational conditions will always create a thermal expansion. Therefore, most gas detection devices based on wavelength modulation spectrometry are limited in their lower detection limits by etalon fringes rather than by electronic noise. Etalon fringe suppression is thus a key element in the increase of the performance (accuracy, precision, detection limit) of a gas detection device.

The state of the art knows several techniques for the suppression of etalon fringes.

The first technique consists in the periodical variation of the position of one of the optical components within the gas detection device, preferentially of a mirror. Such a variation can be implemented for example by placing the mirror onto a piezoelectric positioning device and driving said device by an AC voltage (the frequency of the AC voltage being different from the frequency of wavelength modulation). The overall effect of such an implementation is that the etalon fringes undergo a variation by their full amplitude with time. As long as the time constant of the photo detector's amplifier is significantly higher than the period of the piezoelectric AC drive voltage, the amplifier's output signal will average across all possible etalon fringe amplitudes so that changes in the etalon fringes due to thermal expansion do not have any effect. For any given optical setup, the piezoelectric AC drive voltage can be optimized in frequency and in amplitude in order to maximize the etalon fringe suppression.

A second means to suppress etalon fringes consists in modulating the laser wavelength at a second frequency, which has no relation with the original modulation frequency. In a similar way as in the technique described above, the change of the wavelength due to the second modulation causes a temporal variation of the etalon fringe amplitude, which will be averaged by the photodiode's amplifier, provided that amplifier's time constant is significantly higher than the period of the second wavelength modulation. Similarly, the amplitude and frequency of the second wavelength modulation needs to be optimized for maximum etalon fringe suppression for a given optical arrangement.

Other etalon fringe suppression techniques make use of the slow scan in wavelength of the gas absorption peak (while applying the fast wavelength modulation). Here, etalon fringe amplitude and period are numerically calculated from the obtained scan of the 2f signal, which allows them to be cancelled out. The main drawback of this technique is the necessity to acquire a wavelength scan of the 2f amplifier signal across the gas absorption peak, which implies a very slow measurement cycle.

A common point of all etalon fringe suppression techniques is that there is no absolute suppression technique, and that the main performance limitations of most gas detection devices stem from residual etalon fringes. FIG. 2 shows in diagram (a) residual etalon fringes of an oxygen detector (with zero oxygen concentration) which employs a second, independent wavelength modulation (the residual etalon is about 3 times larger than the electronic noise floor) and in diagram (b) the same device as in (a) with three oxygen absorption peaks.

In view of this, it is the object of the present invention to provide an etalon fringe suppression technique for gas detection, which is less dependent from the temperature and sudden wavelength changes.

Based on this etalon suppression technique it is a further object of the invention to provide a method and device with an easier generation of said first measuring signal which is a function of the intensity of said initial light signal and substantially independent of the concentration of said gas.

SUMMARY OF THE INVENTION

This problem is solved by the gas detection method and the detector device as claimed according to the invention.

According to the invention the gas detection method comprises generating said second measuring signal by determining a first pre-measuring signal when the laser source is operated at the center of the gas absorption peak, a second pre-measuring signal when the laser source is operated with a DC drive current below the gas absorption peak of the gas to be detected, and a third pre-measuring signal when the laser source is operated with a DC drive current above said gas absorption peak, with a difference between said DC drive currents which corresponds to the etalon fringe period determined in a calibration step before; and determining the final second measuring signal as the difference between the first pre-measuring signal and the arithmetic mean of the second pre-measuring signal and the third pre-measuring signal. The present invention is based on the measurement techniques described in the above mentioned prior art document WO 2005/026705 A1 and in the co-pending U.S. patent application Ser. No. 11/227,477. The content of these documents is incorporated by reference as far as technical background and signal treatment is concerned, which might not be described in this description. The present method for etalon suppression can be applied to all the different kinds of generation of measuring signals as mentioned above and described in these documents.

The advantage of this 3-point measurement is that it cancels out the contribution of residual etalon fringes even when these fringes shift their position across the laser dc drive current axis. The stability of the gas detection device against large variations of the ambient temperature is thus greatly enhanced. In respect to a laser current scan of the absorption peak as described above, the 3-point measurements is a considerably faster measurement algorithm.

In case of an etalon fringe generated by a very small cavity, it is not possible to determine the etalon fringe period, as the latter is longer than the tuning wavelength of the laser. In this case, it is sufficient that the off-peak positions are sufficiently far off the gas absorption peak so that latter does not influence the related signals.

Preferably said calibration step is performed by generating a measuring calibration signal without a gas to be determined as a function of the DC laser current and determining said etalon fringe period as the difference between the DC drive currents of extreme values of the same type.

There are three general cases of etalon fringes when regarding their period in wavelength:

etalon fringes with a period shorter or equal than the width of the gas absorption peak;

etalon fringes with a period longer than the width of the gas absorption peak, but shorter than the overall tuning range of the laser;

etalon fringes with a period longer than the overall tuning range of the laser.

Etalon fringes of (1) are generated by optical cavities of several cm (which corresponds to the length of the gas absorption path) and are usually well counter-acted by the technique of additional laser modulation.

Etalon fringes of (2) are generated by cavities of several mm, which typically corresponds to the distance between the laser chip and the window of the laser's header. Such etalon fringes are usually resistant to additional laser modulations and must be counter-acted by tilted laser header windows. However, due to the wide aperture of the laser beam (10-20°), some of the laser light may be back-reflected by the edges of the header's metal cap, or by glue residuals sitting in the edge formed by window and metal cap. The present invention counter-acts such residual etalon fringes very efficiently.

Etalon fringes of (3) stem from optical cavities, which are significantly smaller than 1 mm (typically 100-300 microns). They cannot be addressed by additional laser modulation techniques, as they are rather difficult to identify in the first place. They are typically experienced as a temperature-dependant offset on the 2f signal. In this case, the present invention counter-acts such etalon fringes with a very high efficiency.

According to a preferred embodiment said first measuring signal is generated by determining a first detection signal when the laser source is operated with said DC drive current below said gas absorption peak and a second detection signal when the laser source is operated with said DC drive current above said gas absorption peak, and determining the arithmetic mean of said first detection signal and said second detection signal. The etalon fringe suppression by said three-point measurement as described above allows implementing a substantial simplification of the reference channel. This leads to a simplified method for generating said first measuring signal, which is then further processed as known.

In the gas detector device said first means for providing said first measuring signal receive said detection signal without derivator and is adapted for determining said first measuring signal by calculating the arithmetic mean of a first detection signal, determined when the laser source is operated with a DC drive current below the gas absorption peak of the gas to be detected, and a second detection signal, determined when the laser source is operated with a DC drive current above said gas absorption peak. Both detection signals are determined with a DC drive current without a gas concentration contribution to the detected signal and the difference between the DC drive currents correspond to an etalon fringe period of the optical system of the detection region. In the previous mentioned two patent documents, the reference channel of the laser gas detector consists of a separate lock-in channel which analyses the detector signal either on the modulation frequency f, or on twice the modulation frequency 2f but with a defined phase relation. This lock-in channel is not necessary in the gas detector device of this invention, when, based on the etalon suppression, the first measuring signal is determined accordingly.

The advantages of this method are very straightforward: If the temperature of the laser is not well fixed, the laser DC current needs to be re-adjusted which changes the laser intensity, but not necessarily the f-signal. Under the present invention, the laser intensity is directly measured so that the calibration of the gas detection device remains stable. The measurement of the direct laser intensity has already been addressed by the 2f/2f-measurement in the co-pending U.S. patent application Ser. No. 11/227,477. However, the present 2f/dc measurement is much more simple to implement as it does not require a lock-in channel—it just requires an averaging of the pre-amplified photodiode signal.

BRIEF DESCRIPTION OF THE DRAWINGS

In the following particular features and advantages of the present invention will be described by way of non-limiting embodiments (the single features may be realized alone or together with other in embodiments of the invention) with reference to the annexed drawings, in which.

DETAILED DESCRIPTION

Figure 1:
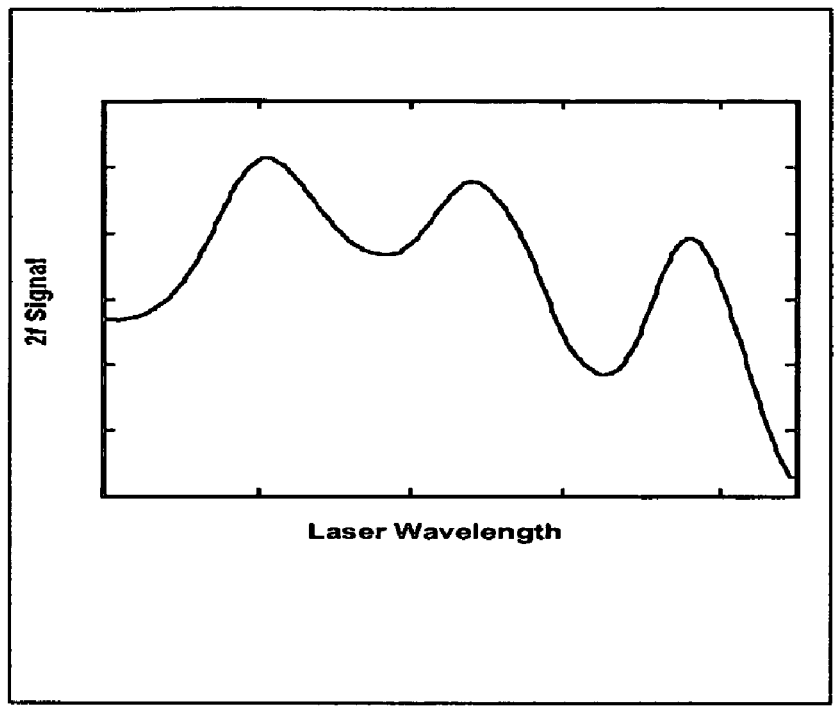
FIG. 1 shows diagrams of (a) etalon fringes of a methane gas detector with zero gas concentration and (b) the same device as in (a) with methane present.
Figure 1:
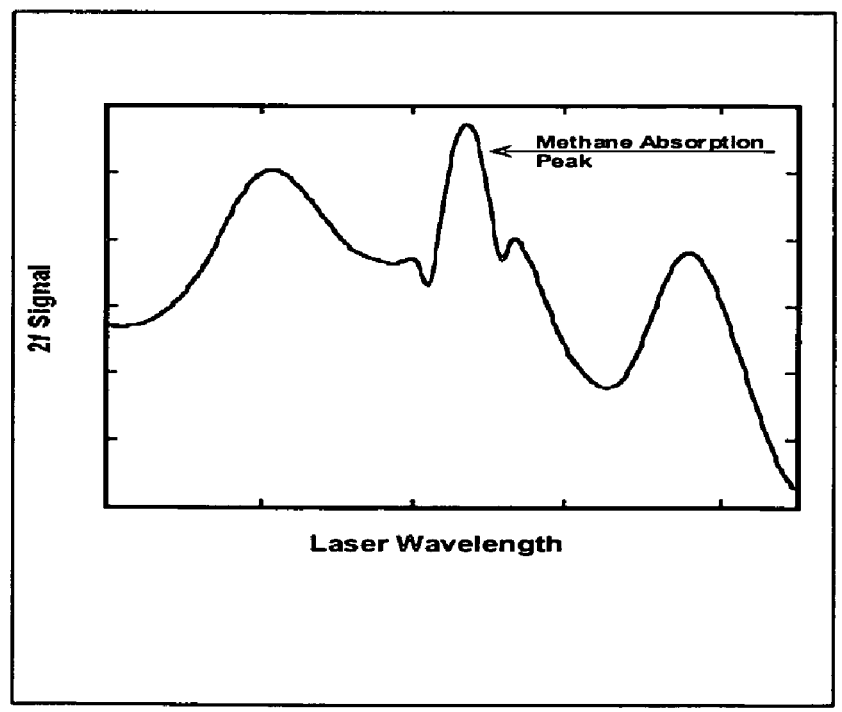
Figure 2:
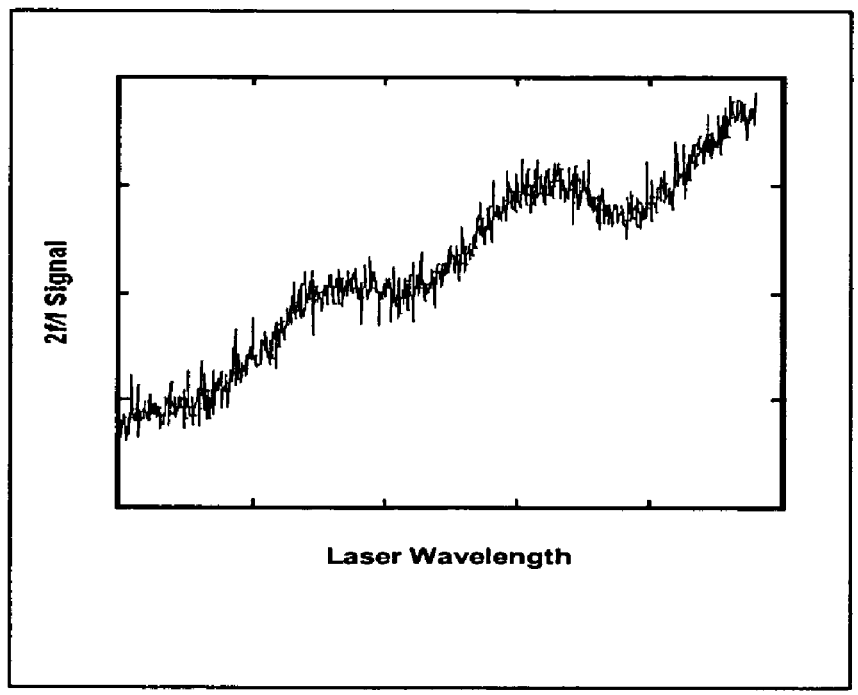
FIG. 2 shows diagrams of (a) residual etalon fringes of an oxygen detector (with zero oxygen concentration) which employs a second, independent wavelength modulation and (b) the same device as in (a) with three oxygen absorption peaks.
Figure 2:
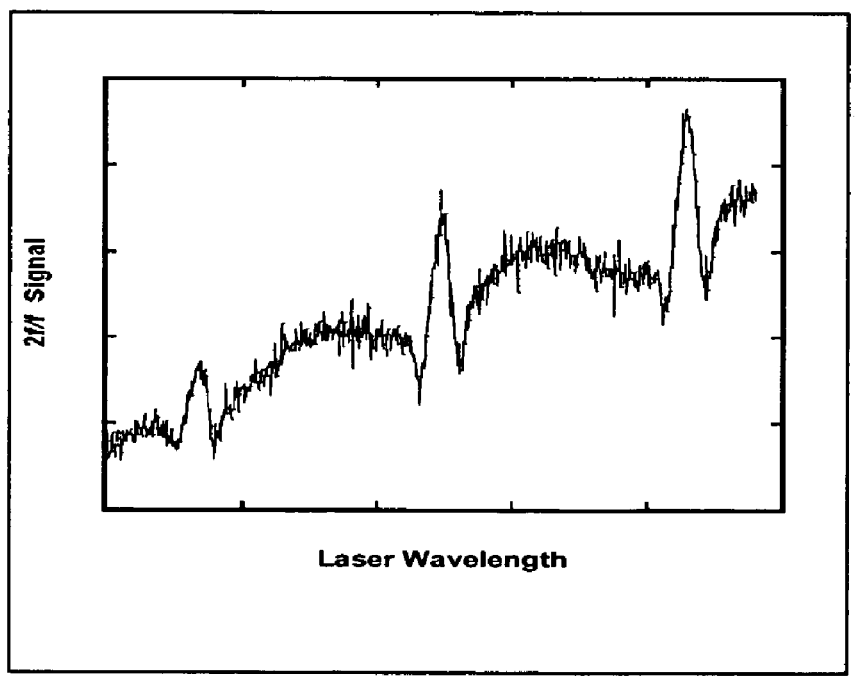

As already discussed the present invention is based on the measurement technique described in two patent documents of the applicant mentioned-above:

A tuneable laser 1 is centered by the appropriate laser DC drive current onto the gas absorption peak of the gas to be measured. The temperature of the laser is usually held at a constant value in order to avoid a wavelength drift of the laser due to a drift in temperature of the laser. An AC current of a frequency f superimposes the DC laser current so that the laser wavelength oscillates around the gas absorption peak with the frequency f.

The laser light is transmitted through a gas volume 4 containing the gas to be measured and is subsequently incident onto a photodiode as detection means. The AC modulation of the laser drive current is connected to an intensity oscillation of the laser's optical output, this intensity oscillation occurring at the modulation frequency f. When the target gas is present in the gas absorption path, part of the laser light will be absorbed each time the laser wavelength coincides with the gas absorption wavelength. As this happens exactly twice per modulation cycle, the signal output of the photodiode receiving the laser light is a combination of a DC signal, an AC signal at the frequency f, and an AC signal at the frequency 2f. The above-mentioned prior art document WO 2005/026705 A1 and the co-pending U.S. patent application Ser. No. 11/227,477 describe a signal treatment, which separate the different contributions of the photodiode signal to obtain information about the laser intensity and the gas concentration.

In the present invention, the measurement of the gas concentration resulting in a measuring signal $S_{MA}$ which is a function of the gas absorption and substantially independent of an intensity modulation of said initial light signal $S_0$ at said initial frequency f is not only performed at the center of the gas absorption peak, but split into three discrete measurements. In a first step during the calibration, the period of the main etalon fringe in respect to the laser DC drive current is determined (FIG. 3a) by generating a measuring calibration signal $S_{MC}$ and determining the etalon fringe period as the difference between the DC drive currents of extreme values of the same type. During the subsequent operation of the gas detection device (FIG. 3b), the laser is operated at the center of the gas absorption peak (0) providing a first pre-measuring signal $S_{M0}$, then at a laser DC drive current to the left (1) of the gas absorption peak providing a second pre-measuring signal $S_{M1}$, and finally at a laser DC drive current to the right (2) of the gas absorption peak providing a third pre-measuring signal $S_{M2}$. The difference in current of the positions (1) and (2) needs to be the etalon fringe period determined as in FIG. 3(a). In the case of short period etalon fringes, this difference can be an integer multiple of the etalon fringe period. The exact position of the off-peak positions (1) and (2) in relation to the etalon fringe period, i.e. whether they are at the fringe maximums, minimums or in-between, is of no relevance.

The gas concentration value is then determined by the measurement signal given by $S_{MA}=S_{M0}-(S_{M1}+S_{M2})/2$.

Figure 3:
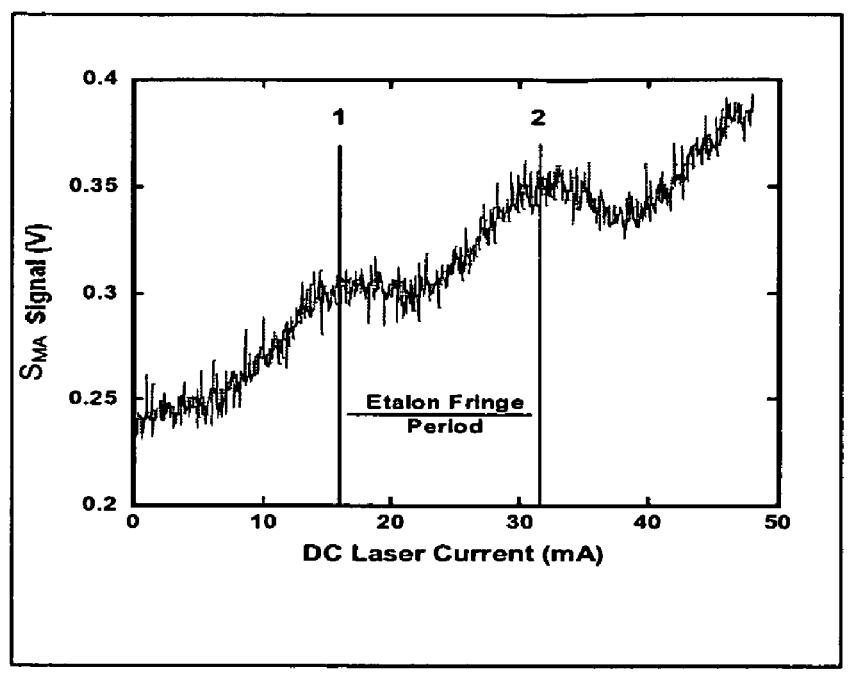
FIG. 3 shows diagrams of (a) the determination of the off-peak measurement points by evaluating the etalon fringe period in terms of laser DC drive current (no target gas present) and (b) the 3-point measurement wherein the signal is measured at the gas absorption peak (0) and at the two off-peak positions (1) and (2) determined in (a)
Figure 3:
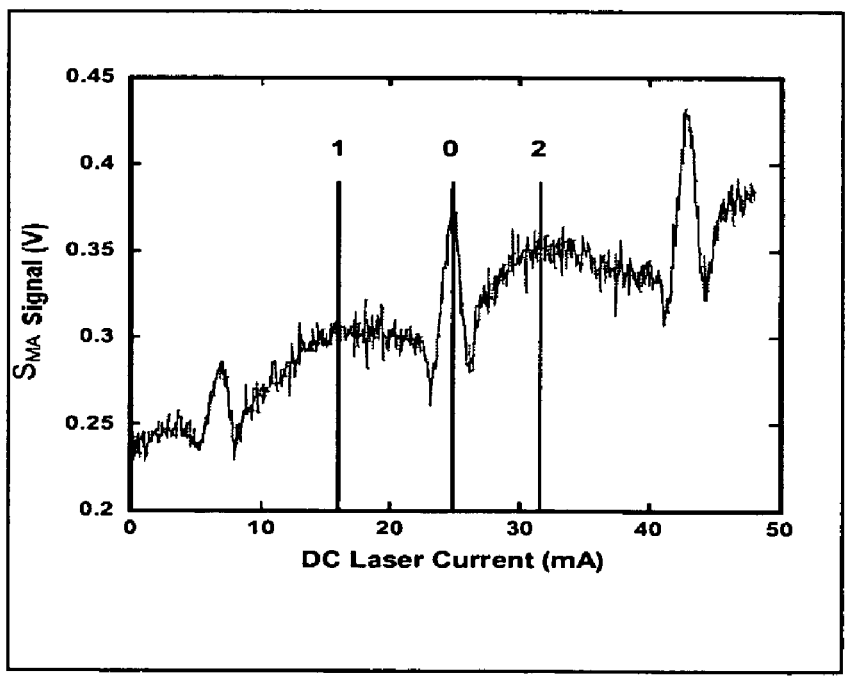

The advantage of this 3-point measurement is that it cancels out the contribution of residual etalon fringes even when these fringes shift their position across the laser DC drive current axis in FIG. 3.

The etalon fringe suppression by a three-point measurement as described above allows implementing a substantial simplification of the reference channel.

Figure 4:
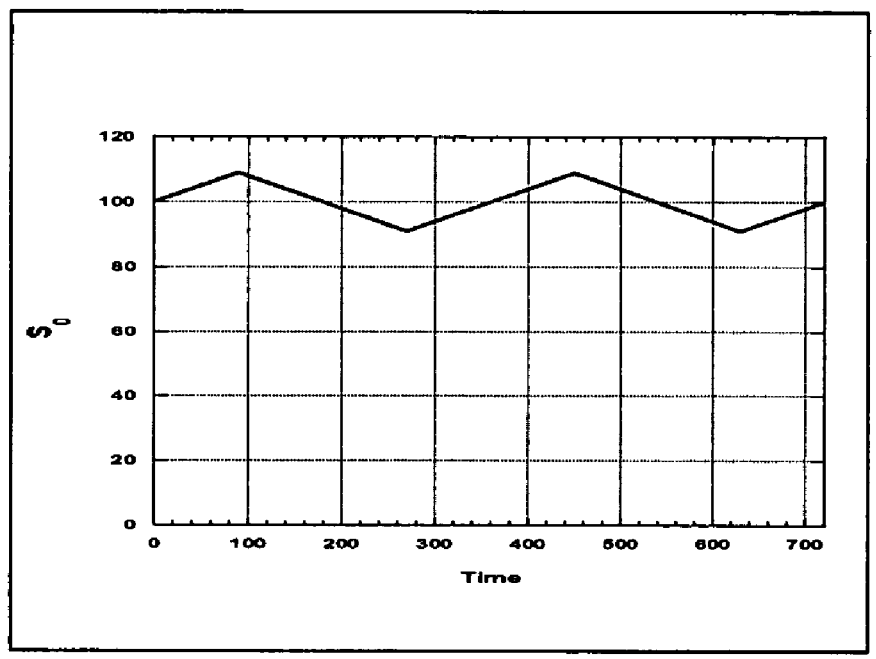
FIG. 4 shows diagrams of (a) the intensity of the light as seen by the photodiode over time when operated off the gas absorption peak and (b) the intensity of the light as seen by the photodiode over time when operated centered onto the gas absorption peak and with gas concentration.
Figure 4:
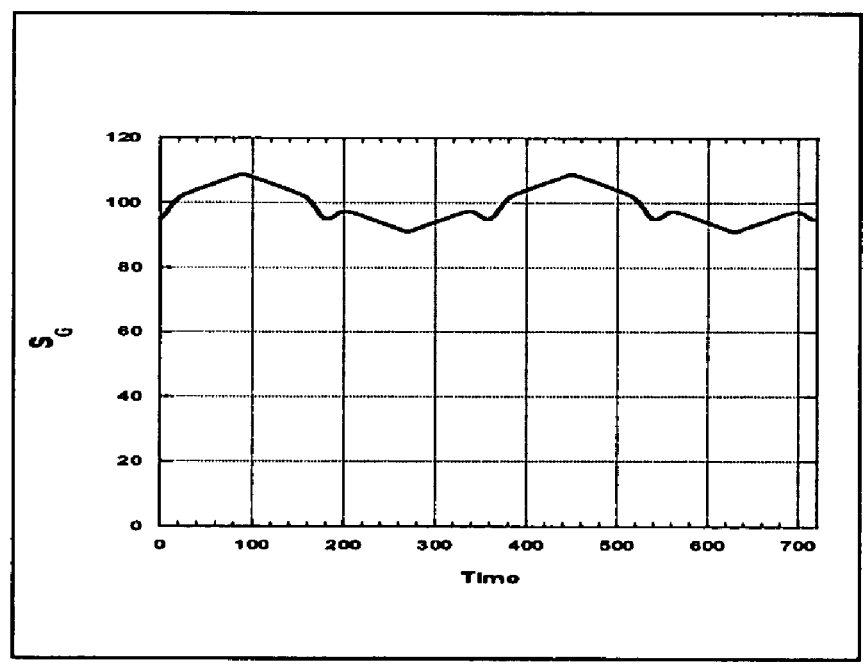

The reference measurement as described in WO 2005/026705 A1 and the co-pending U.S. patent application Ser. No. 11/227,477 is based on the principle that the device always operates at the center of the gas absorption line. With a non-zero target gas concentration, the light intensity incident on the light detector has the general outline as depictured in FIG. 4b, so that a lock-in technique is required to separate gas concentration and laser intensity distributions. In the 3-point measurement technique as described above, the separation can be handled much more easily. The 2f signal is still measured at all three measurement points. However, at the two measurement points (1) and the (2) of the gas absorption peak, there is no gas concentration contribution to the detected signal (FIG. 4a). At these two points, the light intensity can be simply determined by averaging the detector signal over time. Thus the complete measurement routine comprises:

Measurement of the first pre-measuring signal $S_{M0}$ at the frequency 2f at the center of the gas absorption peak signal;

Measurement of the second pre-measuring signal $S_{M1}$ at the frequency 2f at a laser DC drive current to the left (1) of the gas absorption peak which corresponds to a wavelength smaller than the gas absorption peak wavelength;

Measurement of a first detection signal $S_{DC1}$ without gas, which is a function of intensity of the initial light signal $S_0$, at a laser DC drive current to the left (1) of the gas absorption peak;

Measurement of the third pre-measuring signal $S_{M2}$ at the frequency 2f at a laser DC drive current to the right (2) of the gas absorption peak which corresponds to a wavelength greater than the gas absorption peak wavelength;

Measurement of a second detection signal $S_{DC2}$, without gas, which is a function of intensity of the initial light signal $S_0$, at a laser DC drive current to the right (2) of the gas absorption peak.

Due to the signal as shown in FIGS. 3b and 4b, the signal at the DC laser drive current at the position (0) cannot been used for intensity measurement as it is a function of the gas concentration.

Figure 5:
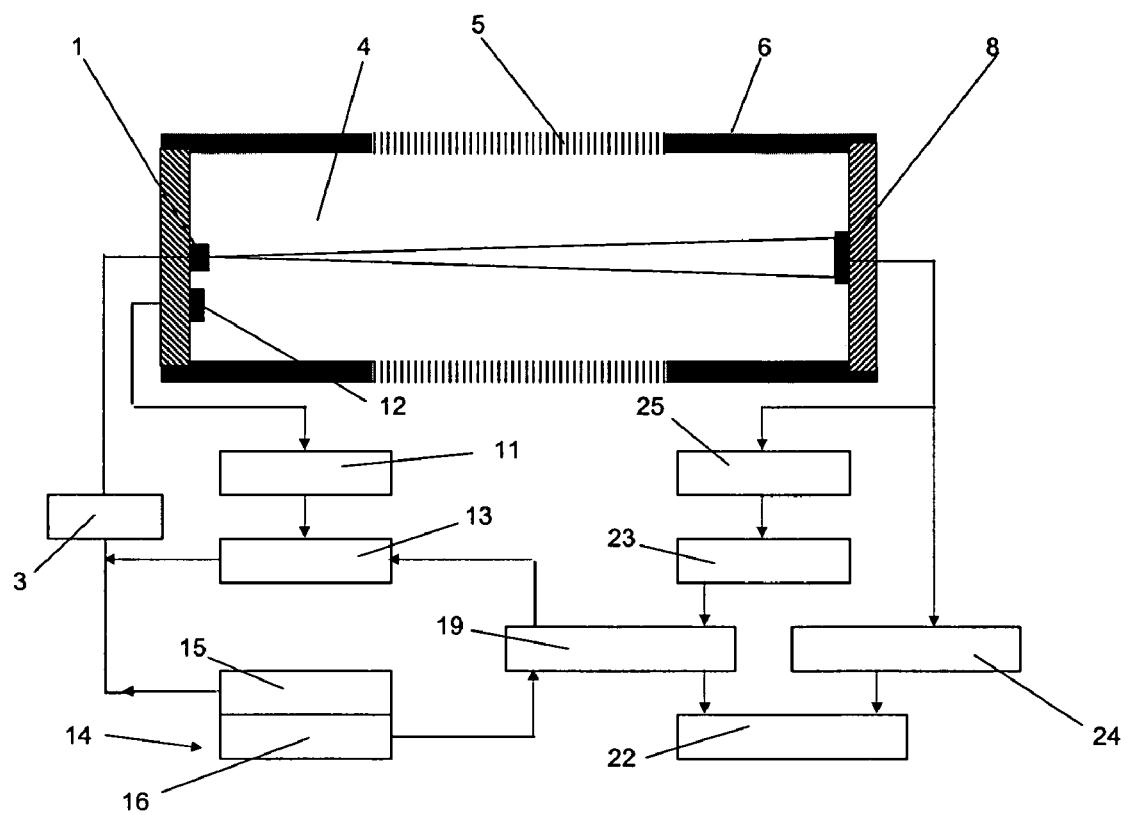
FIG. 5 shows a schematic principle view of an embodiment of the gas detector device according to the present invention using a detection signal directly proportional to the resulting light signal for generating the first measuring signal from said detection signal, which is a function of intensity of said initial light signal.

The final measuring signal $S_M$ being independent from the intensity of light incident onto the detection means gas concentration is then given as $S_M = S_{MA}/S_{MI} = [S_{M0} - (S_{M1} + S_{M2})/2]/[(S_{DC1} + S_{DC2})/2]$ The etalon suppression alone can be performed by and with the gas detector devices described in WO 2005/026705 A1 and the co-pending U.S. patent application Ser. No. 11/227,477. FIG. 5 shows an embodiment of a gas detector device of the invention, which makes use of the etalon suppression and the advantages of the calibration for the etalon suppression. The gas detector device uses a laser source 1 (it can be also more laser sources and respective sensors) arranged in a laser head of a housing 6. This head further might comprise a sealed cell filled with at least one gas for precisely determining the electrical current value to be furnished the source 1 so that the central wavelength of the provided light peak corresponds to the center of the absorption line of the respective gas, as explained here-before and generally known. Finally the head comprises a temperature sensor 12 and if necessary a controlled heater electrically connected to temperature means 11. The housing has a sample chamber or gas detection region 4 with gas inlet 5 for the gas to be detected through which the laser beam provided by the laser source 1 pass through. The light sensor 8 receives the laser beam and provides a resulting signal $S_G$ comprising changes in the intensity of the initial light signal $S_0$ due to the gas concentration in the detection region 4 being direct proportional to the intensity. This resulting signal $S_G$ as detection signal $S_D$ is directed to means for providing the final measuring signal $S_M$.

The gas detector device further comprises electrical supply means 3 for the laser source 1 and DC supply control means 13 for defining a DC current signal for controlling the laser source 1. AC processing means 14 comprise AC supply control means 15 for defining an AC modulation signal at a given reference frequency f generating an alternative scanning around the gas absorption line as explained before. From the AC modulation signal, as known from the prior art, reference modulation signals are generated. The AC processing means further comprise generating means 16 for generating a modulation reference signal $S_{2f}$ on twice the initial modulation frequency f. According to the present invention, the modulation reference signal $S_{2f}$ is provided to a lock-in amplifier 19. The lock-in amplifier 19 also receives a detection signal $S_{DA}$ provided by the light sensor 8 to the lock-in amplifier 19 through the derivator 25, which derivates the detection signal $S_{DA}$ over time, and the preamplifier means 23. In the lock-in amplifier 19 the reference signal is multiplied with detection signal $S_{DA}$ and then integrated over several time periods of the AC modulation signal. The results are the measuring signals $S_{M0}, S_{M1}, S_{M2}$, which are proportional to the gas concentration at the respective positions as seen by the light sensor 8. The measuring signals $S_{M0}, S_{M1}, S_{M2}$ are transmitted to a processing unit 22.

The first detection signal $S_{DC1}$ when the laser source is operated with said DC drive current below said gas absorption peak and the second detection signal $S_{DC2}$ when the laser source is operated with said DC drive current below said gas absorption peak reach the processing unit 22 via preamplifier means 24.

The processing unit 22 determines the final measuring signal $S_M$, which is then given as $S_M = S_{MA}/S_{MI}$ as described above. The final measuring signal $S_M$ considers the etalon fringes and is independent of the laser light intensity.

The invention claimed is:

1. Gas detection method comprising the following steps of providing an initial light signal ($S_0$), by a wavelength modulated laser source (1) driven with a DC drive current;

providing an AC modulation signal at an initial frequency for wavelength modulation of said initial light signal ($S_0$) at said initial frequency (f) symmetrically around an absorption line of a gas the concentration or presence of which is to be determined;

passing said initial light signal ($S_0$) having intensity variations over the time resulting from an alternative scanning around said gas absorption line through a gas detection region (4) intended for receiving at least one of said gases;

receiving a resulting light signal ($S_G$) exciting said gas detection region (4) by detection means (8) providing a detection signal ($S_D$), said resulting light signal ($S_G$) comprises changes in the intensity of the initial light signal ($S_0$) due to the gas concentration in the detection region (4);

generating at least one measuring signal ($S_{MI}$) from said detection signal ($S_D, S_{DC1}, S_{DC2}$), which is a function of intensity of said initial light signal ($S_0$);

generating a second measuring signal ($S_{MA}$), which is a function of the gas absorption and substantially independent of an intensity modulation of said initial light signal at said initial frequency (f), said second measuring signal ($S_{MA}$) is generated by providing a derivated detection signal ($S_{DA}$) substantially proportional to the time derivate of said resulting light signal ($S_G$), multiplying said derivated detection signal ($S_{DA}$) with a second modulation reference signal ($S_{2f}$) at twice of said initial frequency (f) and then integrated over time, whereby the second modulation reference signal ($S_{2f}$) has a defined amplitude level and a defined phase relationship with the intensity variations of said initial light signal ($S_0$), providing a final measuring signal being independent from the intensity of light incident onto the detection means (8) by dividing said second measuring signal ($S_{MA}$) by said at least one measuring signal ($S_{MI}$) and thereby providing a signal relative to the presence or the concentration of a given gas, characterised by generating said second measuring signal ($S_{MA}$) by determining a first pre-measuring signal ($S_{M0}$) when the laser source is operated at the center of the gas absorption peak, a second pre-measuring signal ($S_{M1}$) when the laser source is operated with a DC drive current below the gas absorption peak of the gas to be detected, and a third pre-measuring signal ($S_{M2}$) when the laser source is operated with a DC drive current above said gas absorption peak, with a difference between said DC drive currents which corresponds to the etalon fringe period determined in a calibration step before; and determining the final second measuring signal ($S_{MA}$) as the difference between the first pre-measuring signal ($S_{M0}$) and the arithmetic mean of the second pre-measuring signal ($S_{M1}$) and the third pre-measuring signal ($S_{M2}$).

2. A method according to claim 1, characterised by
performing said calibration step by generating a measuring calibration signal ($S_{MC}$) without a gas to be determined as a function of the DC laser current and determining said etalon fringe period as the difference between the DC drive currents of extreme values of the same type.

3. A method according to claim 1, characterised by
generating said first measuring signal ($S_{MI}$) by determining a first detection signal ($S_{DC1}$) when the laser source is operated with said DC drive current below said gas absorption peak and a second detection signal ($S_{DC2}$) when the laser source is operated with said DC drive current above said gas absorption peak, and determining the arithmetic mean of said first detection signal ($S_{DC1}$) and said second detection signal ($S_{DC2}$).

4. A gas detector device comprising
a least one wavelength modulated laser source (1) providing an initial light signal ($S_0$),
a detection region (4) intended for receiving at least one gas the concentration or presence of which is to be determined,
supply control means (13, 14) for wavelength modulating said initial light signal ($S_0$) at a initial frequency (f) symmetrically around an absorption line of one of said gases and providing said initial light signal ($S_0$) having intensity variation over the time, said supply control means comprise DC supply control means (13) for defining a DC current signal and AC supply control means (14) for defining an AC current signal at said given initial frequency (f) for generating an alternative scanning of light intensity of said initial light signal ($S_0$) around said gas absorption line, a light sensor (8) respectively arranged at the periphery of said detection region (4), said sensor (8) is intended for receiving a resulting light signal ($S_G$) comprising changes in the intensity of the initial light signal ($S_0$) having passed through said detection region (4) and providing a detection signal ($S_D$, $S_{DC1}$, $S_{DC2}$) proportional to the light intensity variation of said resulting light signal ($S_G$), processing means (16-25) for providing from said detection signal ($S_D$) a signal (SA) relative to the presence or the concentration of a given gas in said detection region (4), said processing means comprise means (25) for providing a derivated detection signal ($S_{DA}$) substantially proportional to the time derivate of said resulting light signal ($S_G$), first generating means (18) for generating a first modulation reference signal ($S_f$) at a defined first frequency and second generating means (16) for generating a second modulation reference signal ($S_{2f}$) at twice of said initial frequency (f), both modulation reference signals ($S_f$, $S_{2f}$) have a defined relationship in phase with the intensity variations of said initial light signal ($S_0$), first means (21) for providing a first measuring signal ($S_{MI}$) which is a function of the intensity of said initial light signal ($S_0$) and substantially independent of the concentration of said gas, second means (19) for multiplying said second modulation reference signal ($S_{2f}$) with said detection signal ($S_{D0}$) and then integrating over time in order to provide a second measuring signal ($S_{MA}$) which is a function of the gas absorption and substantially independent of an intensity modulation of said initial light signal ($S_0$) at said initial frequency (f), a processing unit (22) for dividing said second measuring signal ($S_{MA}$) by the first measuring signal ($S_{MI}$) for providing a final measuring signal ($S_M$) relative to the presence of a given gas or to its concentration, characterised in that said first means (21) for providing a first measuring signal ($S_{MI}$) receive said detection signal ($S_D$, $S_{DC1}$, $S_{DC2}$) without derivator and is adapted for determining said first measuring signal ($S_{MI}$) by calculating the arithmetic mean of a first detection signal ($S_{DC1}$), determined when the laser source is operated with a DC drive current below the gas absorption peak of the gas to be detected, and a second detection signal ($S_{DC2}$), determined when the laser source is operated with a DC drive current above said gas absorption peak, each with a DC drive current without a gas concentration contribution to the detected signal and the difference between the DC drive currents correspond to an etalon fringe period of the optical system of the detection region (4).

* * * * *

UNITED STATES PATENT AND TRADEMARK OFFICE
CERTIFICATE OF CORRECTION

PATENT NO. : 7,414,727 B2 Page 1 of 1
APPLICATION NO. : 11/413473
DATED : August 19, 2008
INVENTOR(S) : Bert Willing et al.

It is certified that error appears in the above-identified patent and that said Letters Patent is hereby corrected as shown below:

In column 11, claim 3, line 51, before "least" delete "a" and insert --at--.

In column 11, claim 3, line 57, before "initial frequency" delete "a" and insert --an--.

Signed and Sealed this

Second Day of December, 2008

JON W. DUDAS
*Director of the United States Patent and Trademark Office*